(12) United States Patent
Ohayon

(10) Patent No.: US 12,272,454 B2
(45) Date of Patent: Apr. 8, 2025

(54) ASYNCHRONOUS ADMINISTRATION AND VIRTUAL PROCTORING OF A DIAGNOSTIC TEST

(71) Applicant: BRIGHTERMD LLC, Plano, TX (US)

(72) Inventor: Jesse Ohayon, Plano, TX (US)

(*) Notice: Subject to any disclaimer, the term of this patent is extended or adjusted under 35 U.S.C. 154(b) by 0 days.

(21) Appl. No.: 17/651,828

(22) Filed: Feb. 21, 2022

(65) Prior Publication Data
US 2023/0268083 A1 Aug. 24, 2023

(51) Int. Cl.
| | | |
|---|---|---|
| G16H 40/67 | (2018.01) | |
| A61B 5/00 | (2006.01) | |
| G11B 27/00 | (2006.01) | |
| G16H 10/40 | (2018.01) | |
| G16H 50/20 | (2018.01) | |
| G16H 80/00 | (2018.01) | |
| H04L 65/61 | (2022.01) | |
| H04N 5/76 | (2006.01) | |

(52) U.S. Cl.
CPC ........... G16H 40/67 (2018.01); A61B 5/0002 (2013.01); G11B 27/005 (2013.01); G16H 10/40 (2018.01); G16H 50/20 (2018.01); G16H 80/00 (2018.01); H04L 65/61 (2022.05); H04N 5/76 (2013.01)

(58) Field of Classification Search
CPC ..... G16H 10/00–80/00; H04L 1/00–2463/146; H04N 1/00–2213/008; G11B 3/00–2220/956; A61B 5/0002
See application file for complete search history.

(56) References Cited

U.S. PATENT DOCUMENTS

| | | | | |
|---|---|---|---|---|
| 11,289,196 B1* | 3/2022 | Ferro, Jr. | ............. | A61B 5/7435 |
| 11,369,454 B1* | 6/2022 | Ferro, Jr. | ............... | G16H 40/20 |
| 11,373,756 B1* | 6/2022 | Ferro, Jr. | ............... | G16H 40/63 |
| 2002/0116220 A1* | 8/2002 | Glazier | ................... | G16H 40/20 |
| | | | | 705/2 |
| 2003/0036683 A1* | 2/2003 | Kehr | ...................... | G16H 70/20 |
| | | | | 600/300 |
| 2007/0117083 A1* | 5/2007 | Winneg | ................... | G09B 7/00 |
| | | | | 434/350 |
| 2009/0327691 A1* | 12/2009 | Kishore | ........... | H04N 21/63345 |
| | | | | 713/150 |
| 2010/0322487 A1* | 12/2010 | Geosimonian | .......... | G06F 21/34 |
| | | | | 382/115 |
| 2011/0134203 A1* | 6/2011 | Smelyansky | .......... | G16H 40/67 |
| | | | | 725/78 |

(Continued)

FOREIGN PATENT DOCUMENTS

| | | | | | |
|---|---|---|---|---|---|
| WO | WO-2006001055 A1 | * | 1/2006 | ............... | A61B 5/00 |
| WO | WO-2022019963 A1 | * | 1/2022 | | |
| WO | WO-2022098815 A1 | * | 5/2022 | ............ | B01L 3/5023 |

OTHER PUBLICATIONS

Merittrac, "Online Exam Proctoring," https://web.archive.org/web/20211128030218/https://www.merittrac.com/online-proctoring/online-exam-proctoring. (Year: 2021).*

(Continued)

*Primary Examiner* — Jonathon A. Szumny
(74) *Attorney, Agent, or Firm* — Scheef & Stone, L.L.P.; Keith C. Rawlins, Esq.

(57) ABSTRACT

Asynchronous administration and virtual proctoring of a diagnostic test, where virtual proctoring occurs at a later time and different location than the administration of the diagnostic test.

12 Claims, 2 Drawing Sheets

(56) References Cited

U.S. PATENT DOCUMENTS

| | | | | |
|---|---|---|---|---|
| 2014/0129259 | A1* | 5/2014 | Seriani | G16H 80/00 |
| | | | | 705/3 |
| 2017/0053543 | A1* | 2/2017 | Agrawal | A61B 90/37 |
| 2019/0355457 | A1* | 11/2019 | Lev | G16H 40/20 |
| 2020/0042773 | A1* | 2/2020 | Benkreira | G06V 20/62 |
| 2021/0295725 | A1* | 9/2021 | Jaeh | G09B 7/00 |
| 2021/0326474 | A1* | 10/2021 | Sparks | G06Q 10/10 |
| 2021/0327187 | A1* | 10/2021 | Wisniewski | G16H 10/20 |
| 2021/0391041 | A1* | 12/2021 | White | H04L 9/3231 |
| 2022/0084659 | A1* | 3/2022 | Rowe | G06V 10/56 |
| 2022/0101999 | A1* | 3/2022 | Bonutti | A61N 1/3605 |
| 2022/0310253 | A1* | 9/2022 | Ferro, Jr. | G16H 20/10 |
| 2023/0069802 | A1* | 3/2023 | Kitamura | A61B 5/02042 |

OTHER PUBLICATIONS

Think Exam Admin, "Online Proctoring System—Know about its features and Pros & Cons!," https://thinkexam.com/blog/online-proctoring-system-know-features-pros-cons/. (Year: 2020).*

Online Exams & Proctoring, "Why Live Proctoring is Key to Conducting High-Stake Online Exams," https://blog.talview.com/why-live-proctoring-key-to-conducting-high-stake-online-exams. (Year: 2020).*

"NIH to evaluate COVID_19 at-home testing system," NIH National Institutes of Health—News Releases; Media Advisory, Monday Mar. 1, 2021; https://www.nibib.nih.gov/news-events/newsroom/nih-evaluate-covid-19-home-testing-system. (Year: 2021).*

* cited by examiner

ASYNCHRONOUS ADMINISTRATION AND VIRTUAL PROCTORING OF A DIAGNOSTIC TEST

FIELD

The present disclosure generally relates to diagnostic testing for the presence of a medical condition, and more particularly, to diagnostic tests that require proctoring.

BACKGROUND

Diagnostic testing is used to determine whether a patient has a medical condition. Examples of diagnostic tests include a biopsy, sports doping test, blood pressure test, scans (CAT, CT, MRI), pregnancy tests, and diagnostic tests for the SARS-CoV-2 virus (also known as COVID-19) and its variants.

Two diagnostic tests are predominantly available for diagnosing SARS-CoV-2: a polymerase chain reaction (PCR) test and a rapid test. The PCR test detects the presence of genetic material of the target, e.g., the SARS-CoV-2 virus in a sample taken from a patient's respiratory tract. The PCR test can take hours or days to return a result. The rapid test detects the presence of viral proteins (antigens) expressed by the SARS-CoV-2 virus in a sample taken from a patient's respiratory tract. The rapid test can return a result in minutes, typically less than an hour. The PCR test is viewed by some as more reliable than the rapid test; however, the rapid test gives results much faster than the PCR test.

Current data for infections of SARS-CoV-2 in the United States shows that the number of infections varies over time. When surges in infection rise, so does the demand for diagnostic testing for SARS-CoV-2. In some cases, employers wish to protect their employee ranks by testing employees on a period basis, such as daily, weekly, or some other trigger for testing such as having one or more symptoms of SARS-CoV-2. Some employers, such as those having hundreds and thousands of employees to test, have need for mass SARS-CoV-2 diagnostic testing in a short period of time. Rapid testing has recently become the favored test for mass SARS-CoV-2 diagnostic testing, since the results for rapid testing are available in less than an hour, typically in a matter of minutes.

There is a need for mass diagnostic testing solutions.

SUMMARY

A method for asynchronous administration and virtual proctoring of a diagnostic test, comprising: receiving, by a computer system from an application running on a patient computer device, a video file and a first image file, wherein the video file contains a recording of a patient administering the diagnostic test, wherein the first image file is a photo of a medical device displaying a result of the diagnostic test; sending or streaming, by the computer system to a proctor computer device, the video file and the first image file; and receiving, by the computer system from the proctor computer device, a confirmation result of the diagnostic test. The recording of the video file is recorded beginning at a first point in time, and a virtual proctor views the video file and certifies the confirmation result based on the first image file in a continuous amount of time that begins after the first point in time and ends before the confirmation result is received by the computer system from the proctor computer device.

A method for asynchronous administration and virtual proctoring of a diagnostic test incudes: receiving, by the computer system from an application running on the patient computer device, a video file containing a recording of a patient administering the diagnostic test; and virtually proctoring the recording in the video file. The video file can be received at a first point in time, and virtually proctoring begins at a second point in time that is after the first point in time. A recording in the video file can be recorded beginning at a third point in time, and the first and second points in time begin after the third point in time.

A computer system for asynchronous administration and virtual proctoring of a diagnostic test, comprising: one or more processors; and a memory having instructions stored thereon which cause the one or more processors to: receive, from an application running on a patient computer device, a video file and a first image file, wherein the video file contains a recording of a patient administering the diagnostic test, wherein the first image file is a photo of a medical device displaying a result of the diagnostic test; send or stream, to a proctor computer device, the video file and the first image file; and receive, from the proctor computer device, a confirmation result of the diagnostic test; wherein the recording of the video file begins at a first point in time, wherein a virtual proctor views the video file and certifies the confirmation result based on the first image file in a continuous amount of time that begins after the first point in time and ends before the confirmation result is received by the computer system from the proctor computer device.

A computer system for asynchronous administration and virtual proctoring of a diagnostic test, comprising: one or more processors; and a memory having instructions stored thereon which cause the one or more processors to: receive, from an application running on the patient computer device, a video file containing a recording of a patient administering the diagnostic test; and virtually proctor the recording in the video file. The video file can be received at a first point in time, and virtually proctor begins at a second point in time that is after the first point in time. A recording in the video file can be recorded beginning at a third point in time, and the first and second points in time begin after the third point in time.

Other technical features may be readily apparent to one skilled in the art from the following figures, descriptions and claims.

BRIEF DESCRIPTION OF THE DRAWINGS

For a more complete understanding of this disclosure, reference is now made to the following description, taken in conjunction with the accompanying drawings, in which.

DETAILED DESCRIPTION

Figure 1:
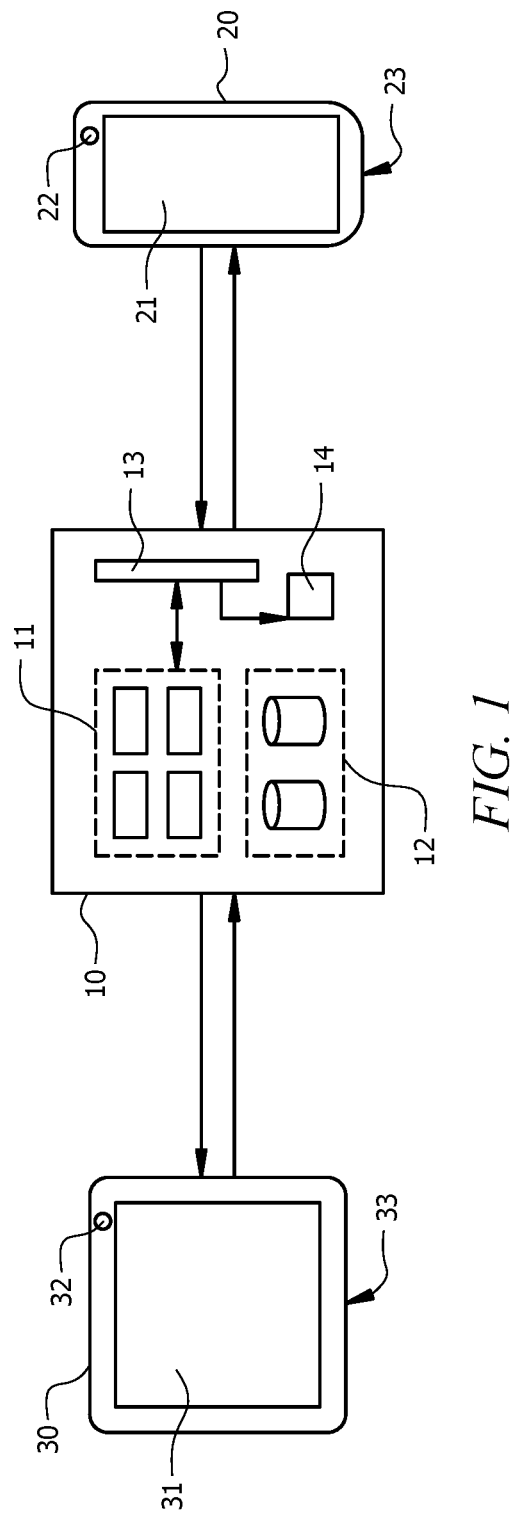
FIG. 1 illustrates a schematic diagram of a computer system configured for virtual proctoring of a diagnostic test.

"Application program" or "application" or "app" as used herein refers to instructions stored on and/or running on a patient computer device, which when executed by a processor of the patient computer device, cause the patient computer device to perform the function(s) of the application disclosed herein.

"Asynchronous" as used herein refers to the non-identical times during which a diagnostic test is administered and during which the diagnostic test is proctored. Non-identical times may be time periods that overlap or non-overlapping time periods.

"Diagnostic test" as used herein refers to a procedure that collects a biological sample from an animal, most typically a human, and analyzes the sample to determine a characteristic (e.g., a medical condition) of the animal. Examples of diagnostic tests include a biopsy, sports doping test, blood pressure test, scans (CAT, CT, MRI), pregnancy tests, diagnostic tests for bacteria, and diagnostic tests for viruses (such as the SARS-CoV-2 virus, also known as COVID-19, and its variants). Diagnostic tests for the SARS-CoV-2 virus include the polymerase chain reaction (PCR) test and the rapid test. Embodiments of diagnostic tests that are utilized in the disclosed method and computer system are administered diagnostic tests (e.g., at-home tests), in which the patient collects their own biological sample.

"High speed" as used herein refers to a playing of a recording in a video file, in a speed that is greater than the speed at which the recording was recorded. High speed can be greater than 1, 2, 3, 4, 5, 5, 6, 7, 8, 9, or 10 times the speed at which the recording was recorded.

"Patient computer device" as used herein refers to a mobile phone (e.g., smartphone), a tablet, a laptop, a desktop, or other computer device configured to having hardware and applications running thereon by which a patient can record video to produce the video file, take one or more photos to produce the image file(s), and send the video file and image file(s) to another computer device.

"Proctor" as used herein refers to a person or device that is qualified under license, regulation, or law to verify that a diagnostic test is correctly administered for or by a patient. A proctor may also be qualified under regulation or law to verify the identity of the patient associated with the diagnostic test.

"Proctor computer device" as used herein refers to a computer device, such as a laptop, desktop, mobile phone (e.g., smartphone), a tablet, or other computer device configured to receive the video file and image file(s) disclosed herein from another computer device, read or display the files for virtual proctoring, and send a proctor input to another computer device.

"Telehealth" or "telemedicine" as used herein refers to medical care conducted virtually online via the Internet or other communication network, between a medical care provider and a patient.

"Virtual proctor" as used herein refers to a person or device that is a proctor and is remotely located from the location at which the diagnostic test is administered to the patient.

"Virtual proctoring" as used herein refers to proctoring, via use of a proctor computer device, a diagnostic test in a location that is remote from the location at which the diagnostic test is administered to the patient.

Disclosed herein is a computer system and method for asynchronous administration and virtual proctoring of a diagnostic test. In the computer system and method, the virtual proctoring is not performed in a live real-time video session with the administration of the diagnostic test. By configuring the computer system and method to dissociate the virtual proctoring from the diagnostic test administration for a patient, it has been unexpectedly found that the number of proctors needed for asynchronous administration and virtual proctoring for diagnostic testing of patients is decreased relative to the number of proctors needed for real-time virtual proctoring. This advantage is multiplied when mass diagnostic testing is needed in a short period of time.

A technical problem associated with the live real-time virtual proctoring of diagnostic tests, as will be described for FIG. 2 utilizing the computer system of FIG. 1, is that each proctor computer device is online and streaming video during the full length of a diagnostic test. The length of the streaming video includes time for the patient to provide the virtual proctor proof of identification, time for administration of the test, and time for results to appear on the medical device of the test kit. For example, a virtual proctor may be connected by video stream to a patient for a SAR-CoV-2 rapid test for a total time of about 20 to 30 minutes. That is, a proctor computer device has to be available for 20 to 30 minutes for the patient to provide the virtual proctor proof of identification, for the virtual proctor to proctor administration of the test, and for the virtual proctor to wait for results to appear on the medical device of the test kit of the SAR-CoV-2 rapid test. Thus, each proctor computer device in live real-time administration and virtual proctoring is connected with a patient computer device for video streaming in a live real-time video session for the virtual proctoring, even during the "dead time" after the test has been administered and before the results are indicated on the medical device. It is estimated that the amount of online video streaming dead time can be over 75% of the total time that the proctor computer device is connected for video streaming with the patient computer device.

The asynchronous virtual proctoring as will be described for FIG. 3 utilizing the computer system of FIG. 1 provides a technical solution for virtual diagnostic testing that 1) allows virtual proctoring and 2) replaces live real-time video streams (2-way video streams, for example, between proctor computer device and patient computer device) with a one-way video communication of a video file from the patient computer device to the computer system and communication of the video from the computer system to a proctor computer device. The technical solution disclosed herein does not use video streaming for virtual proctoring. Instead, a video file is sent from a patient computer device to the computer system, and the computer system can subsequently send or stream the video file to the proctor computer device so that a virtual proctor can (asynchronously at a time later than administration time) view and proctor the administration of the diagnostic test that is played in the recording of the video file. Additionally, because the proctor computer device is not connected to the patient computer device for live real-time two way video streaming, in some embodiments the virtual proctor can cause the proctor computer device to fast forward through the "dead time" in the recording of the video file that is after the test has been administered and before the results are indicated on the medical device.

As such, proctor computer devices in asynchronous administration and virtual proctoring of a diagnostic test do not have to be in live and in real-time with the administration of the diagnostic test as do the proctor computer devices for live real-time video sessions for virtual proctoring. Moreover, because the proctor computer devices for asynchronous administration and virtual proctoring of a diagnostic test do not have to be live and in real-time, the number of proctor computer devices needed to virtually proctor a mass number of tests over a period of time is significantly fewer than the number of proctor computer devices needed for live real-time virtual proctoring for the same mass number of test over the same period of time. The number of proctor computer devices is reduced even further compared to live real-time virtual proctoring in mass diagnostic testing when a virtual proctor can have the proctor computer device fast forward though "dead time" of the proctoring.

FIG. 1 illustrates a schematic diagram of the disclosed computer system 10 configured for virtual proctoring of a diagnostic test. The computer system 10 can be networked with a patient computer device 20 and a proctor computer device 30. While one patient computer device 20 is illustrated for clarity and description, it is contemplated that multiple patient computer devices 20 are networked with the computer system 10 to accomplish mass diagnostic testing according to the disclosure. Likewise, while one proctor computer device 30 is illustrated for clarity and description, it is contemplated that multiple proctor computer devices 30 are networked with the computer system 10 to accomplish mass diagnostic testing according to the disclosure.

Regarding network communication technology, the computer system 10 can be networked with patient computer device 20 and with the proctor computer device 30 via any wired internet connection, wireless internet connection, local area network (LAN), wired intranet connection, wireless intranet connection, or combinations thereof. The networks used for communication between the computer system 10 and the patient computer device 20 can include a Global System for Mobile Communications (GSM), Code-division multiple access (CDMA), General Packet Radio Service (GPRS), Evolution-Data Optimized (EV-DO), Enhanced Data Rates for GSM Evolution (EDGE), Universal Mobile Telecommunications System (UMTS), etc. The networks used for communication between the computer system 10 and the proctor computer device 30 can include a Global System for Mobile Communications (GSM), Code-division multiple access (CDMA), General Packet Radio Service (GPRS), Evolution-Data Optimized (EV-DO), Enhanced Data Rates for GSM Evolution (EDGE), Universal Mobile Telecommunications System (UMTS), etc.

The computer system 10 can include one or more processors, memory, networking cards or interfaces, and other equipment for performing the method and functionality disclosed herein. In embodiments, the computer system 10 can be include multiple computers, located in a brick-and-mortar location, local to the administrator of the computer system 10, in the cloud, or a combination thereof.

In embodiments, the computer system 10 can include a distributed computer architecture, such that hardware is geographically distributed to connect patient computer device 20 with the hardware that is geographically closest to the patient computer device 20 and to connect the proctor computer device 30 with the hardware that is geographically closest to the proctor computer device 30. An advantage of distributed architecture is scalability for mass diagnostic testing for myriad patient computer devices.

In some aspects, the computer system 10 can include computers embodied as servers 11 that are scalable in the cloud, such as those available from Amazon Web Services. The computer system 10 can additionally include one or more databases 12, or clusters of databases 12, configured to store patient information (e.g., patient identification, video file, image file(s), or combinations thereof) received by the cloud servers 11 from the patient computer device 20 (and myriad other patient computer devices), where the databases 12 are accessible by the cloud servers 11 for storage and retrieve of the patient information. Examples of such databases 12 include the scalable database products from MondoDB. The computer system 10 can additionally include a load balancer 13 that is configured to distribute mass patient information received from multiple patient computer devices among the servers 11. The load balancer 13 can be embodied as separate computing device in the computer system 10 (separate from the servers 11), or the load balancer 13 can be embodied as software running on the servers 11. The computer system 10 can additionally include a backend server 14 networked with the load balancer 13 that is configured to track metrics of the computer system 10 for reporting population health and trends in results.

In embodiments, the computer system 10 can include an enterprise grade firewall running on one or more of the servers 11, the load balancer 13, or a combination thereof. In additional or alternative embodiments, the computer system 10 can include private encrypted networking (e.g., one or more virtual private networks (VPNs)) for communications between servers 11 and the load balancer 13 and for communications between servers 11 and the databases 12. In additional or alternative embodiments, the computer system 10 can include a representational state transfer application program interface (REST API) between the load balancer 13 and the firewall. The REST API can aid in embodiments of the computer system 10 where servers 11 are in the cloud functioning as web services for the patient computer device 20.

The patient computer device 20 illustrated in FIG. 1 is embodied as a smartphone; however, the patient computer device 20 can be embodied as another computer device that is within the scope of patient computer device as disclosed herein. In embodiments, the patient computer device 20 can have a screen 21, a camera 22, and a microphone 23. In some embodiments, the patient computer device 20 does not need a microphone and does not engage the microphone when creating the video file for the patient.

The patient computer device 20 is configured to run one or more application programs, including an application program configured to coordinate creation of a video file and image file(s) disclosed herein, and then to send the file(s) to the computer system 10 (as well as other functionality disclosed herein). The application program can be downloaded by the patient computer device 20 from the computer system 10 or other provider for the application program (e.g., Google Play, iTunes, or other provider of apps). Once downloaded, the application program is configured to run on the patient computer device 20 and display interactive screens on the patient computer device 20 to guide a patient to administer a diagnostic test while recording a video of the administration and to take a photo of the medical device that shows the result of the diagnostic test.

The proctor computer device 30 illustrated in FIG. 1 is embodied as a tablet; however, the proctor computer device 30 can be embodied as another computer device that is within the scope of proctor computer device as disclosed herein. In embodiments, the proctor computer device 30 can have a screen 31, a camera 32, and a microphone 33. In some embodiments, such as in some embodiments of asynchronous administration and virtual proctoring of a diagnostic test, the proctor computer device 30 does not need the camera 32 and the microphone 33 and does not engage the camera 32 and microphone 33 when the proctor views the files received from the computer system 10.

In embodiments of live real-time administration and virtual proctoring of a diagnostic test, the proctor computer device 30 is configured to run one or more operating programs or application programs, including a program configured to connect in a 2-way video stream with a patient computer device 20 or the computer system 10 (depending on video conferencing technology), and then to send the results to the computer system 10 (as well as other functionality disclosed herein). The program can be downloaded by the proctor computer device 30 from the computer system 10 or other provider for the application program (e.g., Google Play, iTunes, or other provider of apps). Once downloaded, the program is configured to run on the proctor computer device 30 and display interactive screens on the proctor computer device 30 to allow a proctor to virtually proctor live and in real-time.

In embodiments of asynchronous administration and virtual proctoring of a diagnostic test, the proctor computer device 30 is configured to run one or more operating programs or application programs, including a program configured to receive the video file and image file(s) disclosed herein, and then to send the results to the computer system 10 (as well as other functionality disclosed herein). The program can be downloaded by the proctor computer device 30 from the computer system 10 or other provider for the application program (e.g., Google Play, iTunes, or other provider of apps). Once downloaded, the program is configured to run on the proctor computer device 30 and display interactive screens on the proctor computer device 30 to allow a proctor to view the recording of the video file and the photo(s) of the image file(s) in order to certify the diagnostic test is proctored and to certify the result, and then to send a confirmation result to the computer system 10 after receiving an input from the proctor. In embodiments, the proctor computer device 30 can be configured to display a video control interface on the screen 31 of the proctor computer device 30, such that a virtual proctor can fast forward through at least a portion of the recording, for example, to view the "dead time" of the administration of the diagnostic test in high speed.

Figure 2:
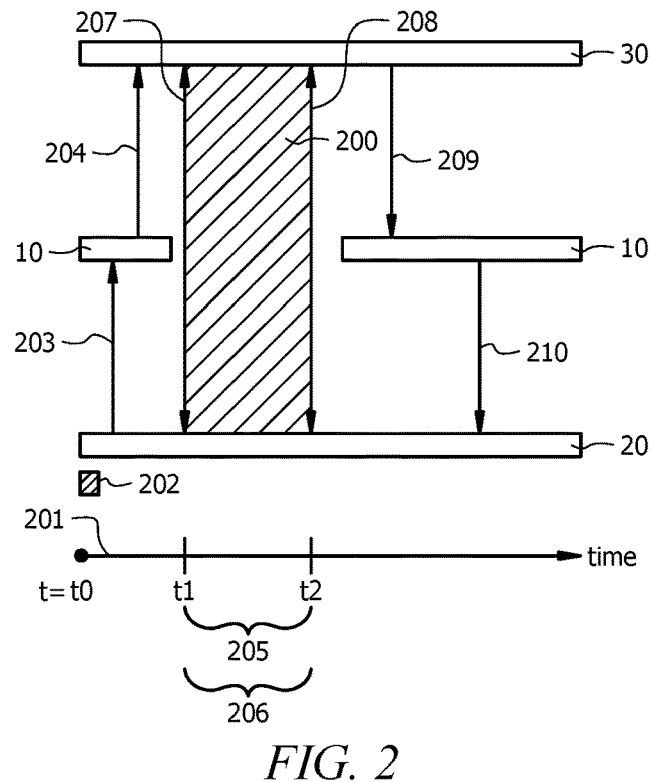
FIG. 2 illustrates a schematic diagram of live real-time administration and virtual proctoring of a diagnostic test.

FIG. 2 illustrates a schematic diagram of live real-time administration and virtual proctoring of a diagnostic test. Virtual proctoring is performed concurrently, in real-time, with administration of the diagnostic test using the patient computer device 20 and the proctor computer device 30 of FIG. 1. The software and applications running on the computer system 10, the patient computer device 20, and the proctor computer device 30 utilize video streaming technology and architecture to provide a real-time video session 200. In embodiments, the software and applications running on the computer system 10, the patient computer device 20, and the proctor computer device 30 can utilize multimedia routing or decentralized video conferencing by which the computer system 10 can match a patient computer device 20 with a proctor computer device 30, and the devices 20 and 30 connect directly (without the computer system 10 in between) via one or more networks disclosed herein for a live real-time video session 200 between the devices 20 and 30, during which the diagnostic test is simultaneously (real-time) administered by the patient while in view of a camera on the patient computer device 20 and proctored by the proctor viewing the video stream on a display of the proctor computer device 30. Alternatively, the software and applications running on the computer system 10, the patient computer device 20, and the proctor computer device 30 can utilize the computer system 10 as a multipoint control unit (MCU) by which the computer system 10 can receive and present the video streams from and to the patient computer device 20 and the proctor computer device 30.

A time axis 201 is included in FIG. 2 to describe the order of communications between the computer system 10 and the patient computer device 20, and between the computer system 10 and the proctor computer device 30. Time t=0 on the time axis 201 represents when a patient begins interacting with the patient computer device 20 to perform the diagnostic test. Point in time t1 occurs after time t=0 and point in time t2 occurs after point in time t1.

At time t=0, the patient can begin interacting with an application running on the patient computer device 20 to enter patient identification information, such as by entering patient identification information into the application, or by having the patent computer device 20 take a photo of an identification card or other proof of patient identity. The patient computer device 20 can be configured to save the photo as an image file 202. The patient identification information, the image file 202, or both can be sent by the application on the patient computer device 20 to, and received by, the computer system 10 in patient information data package 203.

The computer system 10 can select a proctor computer device 30 and send a request data packet 204 containing a request for virtual proctoring and the patient information to the proctor computer device 30. An application or program running on the proctor computer device 30 can directly connect with the application running on the patient computer device 20 to initiate a video session 200 at time t1. The proctor and patient can communicate during the video session 200 such that administration of a diagnostic test by the patient is viewed (proctored) by the proctor on the proctor computer device 30. That is, the administering phase 205 of the diagnostic test occurs in real-time with the virtual proctoring phase 206. The double-headed arrows 207 and 208 indicate the video streams are sent by and received by each of the patient computer device 20 and the proctor computer device 30.

FIG. 2 illustrates that the real-time video session 200 begins at a first point in time t1 and ends at a second point in time t2. Both the administration of the diagnostic test and the virtual proctoring of the diagnostic test occur between the first point in time t1 and the second point in time t2 because virtual proctoring occurs simultaneously in real-time with the administration of the diagnostic test during video session 200. Virtual proctoring begins at the same point in time as the administration of the diagnostic test begins. Likewise, virtual proctoring ends at the same point in time as the administration of the diagnostic test ends.

The live real-time virtual proctoring in FIG. 2 requires a virtual proctor to be available to observe the diagnostic test when the patient is available.

Figure 3:
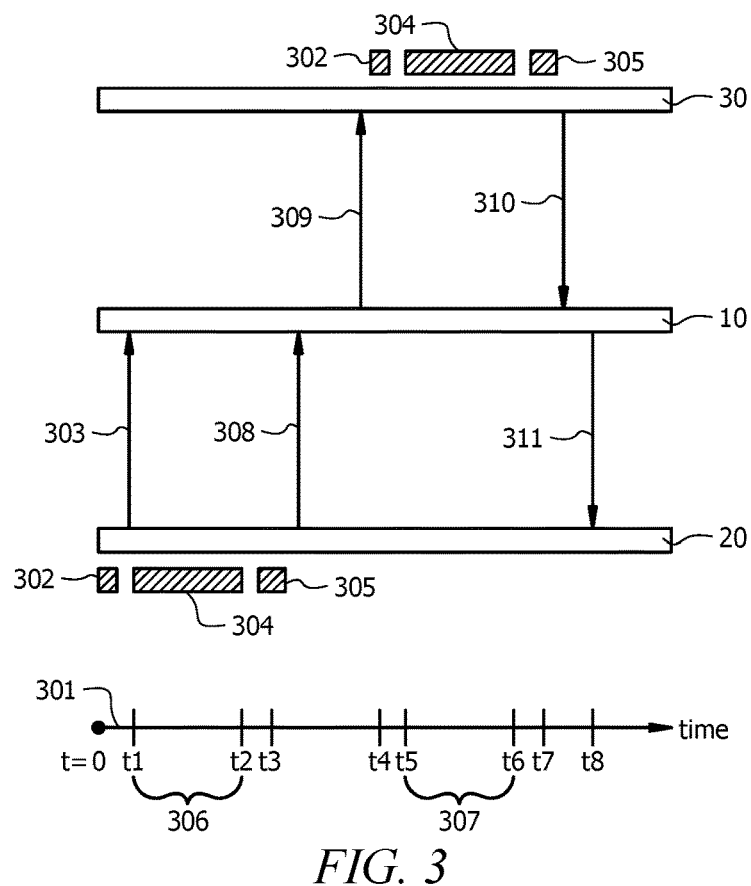
FIG. 3 illustrates a schematic diagram of asynchronous administration and virtual proctoring of a diagnostic test.

FIG. 3 illustrates a schematic diagram of asynchronous administration and virtual proctoring of a diagnostic test. Diagnostic testing with virtual proctoring is performed asynchronously relative to the time that the diagnostic test is administered.

The asynchronous diagnostic test administration and virtual proctoring can be performed using the computer system 10, the patient computer device 20, and the proctor computer device 30. The software and applications running on the computer system 10, the patient computer device 20, and the proctor computer device 30 do not utilize multimedia videoconference routing or decentralized video conferencing for direct connection of video streams between the patient computer device 20 and the proctor computer device 30 because video streaming from the patient computer device 20 is not utilized for asynchronous administration and virtual proctoring of a diagnostic test. All communications of the patient computer device 20 are received by the computer system 10, and the patient computer device 20 and the proctor computer device 30 are not directly connected for video streaming of the diagnostic test.

A time axis 301 is included in FIG. 3 to describe the order of communications between the computer system 10 and the patient computer device 20, and between the computer system 10 and the proctor computer device 30. Time t=0 on the time axis 301 represents when a patient begins interacting with the patient computer device 20 to perform the diagnostic test. Point in times t1, t2, t3, t4, t5, t6, t7, and t8 are illustrated on the time axis 301 for description of the asynchronous administration and virtual proctoring of a diagnostic test. Point in time t1 occurs after time t=0, point in time t2 occurs after point in time t1, point in time t3 occurs after point in time t2, point in time t4 occurs after point in time t3, point in time t5 occurs after point in time t4, point in time t6 occurs after point in time t5, point in time t7 occurs after point in time t6, and point in time t8 occurs after point in time t7.

At time t=0, the patient can begin interacting with an application running on the patient computer device 20 to enter patient identification information, such as by entering patient identification information into the application, or by having the patent computer device 20 take a photo of an identification card or other proof of patient identity. The patient computer device 20 can be configured to save the photo as an image file 302. In embodiments, the patient identification information, the image file 302, or both can be sent by the application on the patient computer device 20 to, and received by, the computer system 10 in patient information data package 303. Alternatively, the patient identification information, the image file 302, or both can be sent by the application on the patient computer device 20 to, and received by, the computer system 10 along with the video file 304 and image file 305 (discussed in more detail below).

The application running on the patient computer device 20 can interact with the patient to generate or create the video file 304 containing a recording of the patient administering the diagnostic test. The recording can begin at point in time t1 and end at point in time t2. In some embodiments, the application running on the patient computer device 20 can be configured to store the video file 304 in a memory or cache of the patient computer device 20. The recording of the video file 304 with the patient computer device 20 is illustrated in FIG. 3 as the administration phase 306, which is the amount of time that elapses between point in time t1 and point in time t2, and is separate from the virtual proctoring phase 307 (described in more detail below).

At point in time t3, the application running on the patient computer device 20 can additionally interact with the patient to generate or create an image file 305 containing a photo of the medical device (e.g., a wand, cartridge for a swab, or housing for a swab) that displays the result of the diagnostic test. For example, the medical device can have a display that shows one line for a negative result or two lines for a positive result, and the photo can capture an image of the display. Alternatively, the medical device can change color depending on whether the result is a positive result, a negative result, or an inconclusive result, and the photo can capture an image of the display.

After point in time t3, a diagnostic test data package 308 containing the video file 304 and the image file 305 can be sent by the application on the patient computer device 20 to, and received by, the computer system 10. In some embodiments, the diagnostic test data package 308 can also include the image file 302 and optionally patient identification information, and in such embodiments, the patient information data package 303 is not utilized since the image file 302 is sent to, and received by, the computer system 10 in the diagnostic test data package 308.

Unlike the live real-time video session in FIG. 2, in FIG. 3 there is no video stream received from or sent to the patient computer device 20 for the administration of the diagnostic test. Because the asynchronous administration and virtual proctoring in FIG. 3 does not have a live real-time video session, one or more of the following apply to the asynchronous administration and virtual proctoring in FIG. 3: the computer system 10 does not receive the video file in a video stream from the patient computer device 20, the computer system 10 does not receive a video stream from the patient computer device 20, the computer system 10 does not receive a video stream from the proctor computer device 30, the computer system 10 does not send a video stream to the patient computer device 20, the patient computer device 20 and the proctor computer device 30 do not exchange video streams, the patient computer device 20 does not send a video stream to the proctor computer device 30, and the proctor computer device 30 does not send a video stream to the patient computer device 20. The only video streaming that may occur in some embodiments during the asynchronous administration and virtual proctoring in FIG. 3 is the computer system 10 video streaming the video file and optionally the image file(s) (photo of patient identification, photo of medical device showing testing result, or both) to the proctor computer device 30.

After receiving the diagnostic test data package 308 at point in time t3, the computer system 10 can select a proctor computer device 30 and send, at point in time t4, a proctor data package 309 containing the image file 302, the video file 304, and the image file 305 to the application or program running on the selected proctor computer device 30.

At point in time t5, the virtual proctor can begin the virtual proctoring phase 307 by viewing the recording on the video file 304 on the proctor computer device 30. The proctor computer device 30 is configured to process the video file 304 and play the recording on the screen 31 of the proctor computer device 30. The virtual proctor continuously views the recording on the video file 304 for a continuous amount of time that elapses between point in time t5 and point in time t6. The virtual proctoring phase 307 ends when the virtual proctor finishes viewing the recording at point in time t6. The time axis 301 illustrates that points in time t5 and t6, indicating the beginning and end of the virtual proctoring phase 307, both occur after points in time t1 and t2, indicating the beginning and end of the administration phase 306.

In alternative embodiments, after receiving the diagnostic test data package 308, the computer system 10 can select a proctor computer device 30 and be configured to, at point in time t4, video stream the recording on the video file 304, the image file 305, or both the video file and the proctor computer device 30. At point in time t5 (which can be the same as point in time t4), the virtual proctor can begin the virtual proctoring phase 307 by viewing the video stream on the proctor computer device 30. The virtual proctor can continuously view the video stream for a continuous amount of time that elapses between point in time t5 and point in time t6. The virtual proctoring phase 307 ends when the virtual proctor finishes viewing the video stream at point in time t6.

In either embodiments described above (i.e., viewing the downloaded recording of the video file 304 or viewing a video stream of the recording of the video file 304), it is contemplated that the proctor computer device 30 can be configured to display a video control interface on the screen 31 of the proctor computer device 30, such that the virtual proctor viewing the recording can fast forward through at least a portion of the recording, for example, to view the "dead time" of the administration of the diagnostic test in high speed. For example, the time between physical administration of the diagnostic test to the patient and the indication of the results can be "dead time" where there is no patient or other activity in the recording. In these embodiments, the proctor computer device 30 can be configured to allow the virtual proctor to fast forward through the dead time in the recording by interacting with the video control interface on the screen 31 of the proctor computer device 30 (e.g., pressing a virtual fast-forward button on the screen 31, followed by pressing the virtual play button on the screen 31). It is contemplated that the fast forwarding can occur during the continuous amount of time that that elapses between point in time t5 and point in time t6 during the virtual proctoring phase 307. In embodiments, fast forwarding can cause the recording to play at a high speed, where high speed can be greater than 1, 2, 3, 4, 5, 5, 6, 7, 8, 9, or 10 times the speed at which the recording was recorded. In embodiments, high speed is 2 times the speed at which the recording was recorded; alternatively, high speed is 4 times the speed at which the recording was recorded; alternatively, high speed is 8 times the speed at which the recording was recorded; alternatively, high speed is 10 times the speed at which the recording was recorded; alternatively, high speed is 15 times the speed at which the recording was recorded; alternatively, alternatively, high speed is 20 times the speed at which the recording was recorded.

The time axis 301 illustrates that points in time t5 and t6, indicating the beginning and end of the virtual proctoring phase 307, both occur after points in time t1 and t2 (point in time t1 and t2 indicating the beginning and end of the administration phase 306, respectively). The virtual proctoring phase 307 can be considered asynchronous with the administration phase 306 because i) point in time t5 is after point in time t1, ii) point in time t5 is after point in time t2, iii) point in time t6 is after point in time t1, iv) point in time t6 is after point in time t2, or v) combinations thereof.

At point in time t7, the virtual proctor can view the image file 305 of the result of the diagnostic test, in order to determine if the result is a positive result, a negative result, or an inconclusive result. The proctor can perform other tasks such as to confirm the diagnostic test was successfully proctored according to requirement and/or regulation, and associate the identity of the patient with the diagnostic test that was virtually proctored. The virtual proctor can input the result of the diagnostic test, also referred to herein as the confirmation result, and any other information related to the virtual proctoring, into the proctor computer device 30, for example, via the screen 31 of the proctor computer device 30.

In embodiments, during the virtual proctoring phase 307, the proctor can interact with the proctor computer device 30 to review the patient identification information, the image file 302, or both (depending upon which information is received from the computer system 10), and the virtual proctor can input into the proctor computer device 30: 1) an association of a) the patient identifier, the information in the image file 302, or both with b) the confirmation result and any other information related to the virtual proctoring; and 2) the confirmation result and any other information related to the virtual proctoring. In additional embodiments, the virtual proctor can input into the proctor computer device 30: an association of a) the patient identifier, the information in the image file 302, or both with b) the video file 304, the image file 305, or both. In alternative embodiments, the proctor can input into the proctor computer device 30 the proctor can interact with the proctor computer device 30 to review the patient identification information, the image file 302, or both (depending upon which information is received from the computer system 10), and the proctor can input into the proctor computer device 30: 1) the patient identifier, the information in the image file 302, or both; and 2) the confirmation result and any other information related to the virtual proctoring.

The computer system 10 can receive a confirmation data package 310 comprising the confirmation result from the proctor computer device 30. In embodiments, the application or program running on the proctor computer device 30 can be configured to send to the computer system 10 in the confirmation data package 310 containing: 1) the confirmation result and any other information related to the virtual proctoring, and 2) an association of a) the patient identifier, the information in the image file 302, or both with b) the confirmation result and any other information related to the virtual proctoring. In alternative embodiments, the application or program running on the proctor computer device 30 can be configured to send to the computer system 10 in the confirmation data package 310 containing: 1) the patient identifier, the information in the image file 302, or both; and 2) the confirmation result and any other information related to the virtual proctoring. In this alternative embodiment, the computer system 10 can associate a) the patient identifier, the information in the image file 302, or both with b) the confirmation result and any other information related to the virtual proctoring. In additional alternative embodiments, the computer system 10 can associate a) the patient identifier, the information in the image file 302, or both with b) the video file 304, the image file 305, or both.

At time t8, the computer system 10 can send to a notification 311 containing the confirmation result to the application running on the patient computer device 20. The application running on the patient computer device 20 can process the notification 311 and then notify the patient of the result of the diagnostic test.

In the asynchronous administration and virtual proctoring of the diagnostic test in FIG. 3, the recording in the video file 304 is recorded beginning at a first point in time t1, and a proctor views the video file 304 and certifies the confirmation result based on the image file 305 in a continuous amount of time (e.g., the virtual proctoring phase 307) that begins after than first point in time t1 and ends before the confirmation result is received by the computer system 10 from the proctor computer device 30. In embodiments, the recording in the video file 304 ends being recorded at point in time t2, and the continuous amount of time begins after the point in time t2. In additional embodiments, the continuous amount of time begins after the proctor computer device 30 receives the proctor data package 309 from the computer system 10.

The disclosed method(s) and computer system 10 have advantages when mass diagnostic testing is needed. The method is performed and the computer system 10 can be utilized for mass diagnostic testing such that a number of virtual proctors needed for asynchronous administration and virtual proctoring during a period of time is less than a number of virtual proctors needed for live real-time virtual proctoring during the period of time. In embodiments, the number of proctors needed for asynchronous administration and virtual proctoring during a period of time is less than 100%, 90%, 80%, 70%, 60%, 50%, 40%, 30%, or 20% of a number of proctors needed for live real-time virtual proctoring during the period of time.

Embodiments of methods in accordance with this disclosure are described with reference to components in FIGS. 1 and 3.

A method for asynchronous administration and virtual proctoring of a diagnostic test, comprising: receiving, by a computer system 10 from an application running on a patient computer device 20, a video file 304 and a first image file 305; sending or streaming, by the computer system 10 to a proctor computer device 30, the video file 304 and the first image file 305; and receiving, by the computer system 10 from the proctor computer device 30, a confirmation result of the diagnostic test. The video file 304 contains a recording of a patient administering the diagnostic test, and the first image file 305 is a photo of a medical device displaying a result of the diagnostic test. The recording of the video file 304 is recorded beginning at a first point in time t1. A virtual proctor views the video file 304 and certifies the confirmation result based on the first image file 305 in a continuous amount of time that begins after the first point in time t1 and ends before the confirmation result is received by the computer system 10 from the proctor computer device 30. The method can also include sending, by the computer system 10 to the application running on the patient computer device 20, a notification 311 containing the confirmation result of the diagnostic test. The method can also include additional functionality of the computer system 10, patient computer device 20, and proctor computer device 30 disclosed herein. The method can also include any aspect and embodiment associated with the functionality of the computer system 10, patient computer device 20, and proctor computer device 30 disclosed herein.

A method for asynchronous administration and virtual proctoring of a diagnostic test incudes: receiving, by the computer system 10 from an application running on the patient computer device 20, a video file 304 containing a recording of a patient administering the diagnostic test; and virtually proctoring the recording in the video file 304. The video file can be received at a first point in time t3, and virtually proctoring begins at a second point in time t5 that is after the first point in time t3. A recording in the video file 304 can be recorded beginning at a third point in time t1, and the first and second points in time t3 and t5 begin after the third point in time t1. The method can also include sending, by the computer system 10 to the application running on the patient computer device 20, a notification 311 containing the confirmation result of the diagnostic test. Virtually proctoring can include any of the functionality of the computer system 10 and proctor computer device 30 described for FIG. 3 between point in time t4 and point in time t7. The method can also include additional functionality of the computer system 10, patient computer device 20, and proctor computer device 30 disclosed herein. The method can also include any aspect and embodiment associated with the functionality of the computer system 10, patient computer device 20, and proctor computer device 30 disclosed herein.

EXAMPLES

The following examples are prophetic examples for virtual proctoring of a SARS-CoV-2 rapid test as the diagnostic test.

Prophetic Example 1

Prophetic Example 1 will utilize live real-time administration and virtual proctoring of SARS-CoV-2 rapid tests as the diagnostic tests. In Prophetic Example 1, 150,000 diagnostic tests will be required to be administered and proctored within one 60-hour work week. Each virtual proctor will proctor one diagnostic test at a time, with total time per proctored diagnostic test (from beginning of administration to a result indicated on the medical device and communicated to the proctor) being 20 minutes.

In the real-time administration and virtual proctoring of Prophetic Example 1, each proctor will virtually proctor 3 diagnostic tests per hour. In a 60-hour work week, each proctor will virtually proctor 180 diagnostic tests.

Using live real-time administration and virtual proctoring as described in FIG. 2 for virtually proctoring one diagnostic test at a time, virtually proctoring the administration of 150,000 diagnostic tests within one 60-hour work week will require 834 proctors to be available, necessitating 834 proctor computer devices to virtually proctor 150,000 diagnostic tests within one 60-hour work week.

Prophetic Example 2

Prophetic Example 2 will utilize asynchronous administration and virtual proctoring of SARS-CoV-2 rapid tests as the diagnostic tests. In Prophetic Example 2, 150,000 diagnostic tests will be required to be administered and proctored within one 60-hour work week, the same as Prophetic Example 1. Each virtual proctor will monitor one proctor computer device at a time, the same as Prophetic Example 1.

In Prophetic Example 2, each proctor will view a portion of the recording on a video file of each diagnostic test in high speed using the proctor computer device. That is, the proctor can fast forward, using controls on the proctor computer device, through the portion of the recording on the video file that is after administration of the diagnostic test and before the result is indicated on the medical device (while the patient is merely waiting for results). Moreover, each proctor will view the recording on the video file at a point in time that is later than when the patient generated the recording on the video file. The total time per proctored diagnostic test (from beginning of administration to a result indicated on the medical device) will be 3 minutes.

Thus, in the asynchronous administration and virtual proctoring of Prophetic Example 2, each proctor will virtually proctor twenty diagnostic tests per hour. In a 60-hour work week, each proctor will virtually proctor 1,200 diagnostic tests.

Using asynchronous administration and virtual proctoring as described in FIG. 3 for virtually proctoring one diagnostic test at a time, virtually proctoring the administration of 150,000 diagnostic tests within one 60-hour work week will require 125 proctors to be available, necessitating 125 proctor computer devices to virtually proctor 150,000 diagnostic tests within one 60-hour work week.

Prophetic Example 3

Prophetic Example 3 will utilize asynchronous administration and virtual proctoring of SARS-CoV-2 rapid tests as the diagnostic tests. In Prophetic Example 3, 150,000 diagnostic tests will be required to be administered and proctored within one 60-hour work week, the same as Prophetic Examples 1 and 2. Each virtual proctor will monitor one proctor computer device at a time, the same as Prophetic Examples 1 and 2.

In Prophetic Example 3, each proctor will view a portion of the recording on a video file of each diagnostic test in high speed using the proctor computer device. That is, the proctor can fast forward, using controls on the proctor computer device, through the portion of the recording on the video file that is after administration of the diagnostic test and before the result is indicated on the medical device (while the patient is merely waiting for results). Moreover, each proctor will view the recording on the video file at a point in time that is later than when the patient generated the recording on the video file. The total time per proctored diagnostic test (from beginning of administration to a result indicated on the medical device) will be 1 minute.

Thus, in the asynchronous administration and virtual proctoring of Prophetic Example 3, each proctor will virtually proctor sixty diagnostic tests per hour. In a 60-hour work week, each proctor will virtually proctor 3,600 diagnostic tests.

Using asynchronous administration and virtual proctoring as described in FIG. 3 for virtually proctoring one diagnostic test at a time, virtually proctoring the administration of 150,000 diagnostic tests within one 60-hour work week will require 42 proctors to be available, necessitating 42 proctor computer devices to virtually proctor 150,000 diagnostic tests within one 60-hour work week.

The number of virtual proctors required in Prophetic Example 2 will be 125 and in Prophetic Example 3 will be 42, while the number of virtual proctors required in Prophetic Example 1 will be 833. The number of proctors in Prophetic Example 2 is only about 15% of the number of proctors in Prophetic Example 1, and the number of proctors in Prophetic Example 3 is only about 5% of the number of proctors in Prophetic Example 1. Thus, the reduction in the number of proctors and the number of proctor computer devices in Prophetic Examples 2 and 3 is significant compared to the number of proctor personnel and proctor computer devices in Prophetic Example 1.

Moreover, it is surprising, unexpected, and counterintuitive that live real-time virtual proctoring would have greater proctor and proctor computing device requirements than asynchronous virtual proctoring. It is believed that asynchronous virtual proctoring greatly reduces proctoring dead time (e.g., waiting for patient to fumble around with identification, waiting for results after administration of the diagnostic test) because proctors in asynchronous administration and virtual proctoring do not have to proctor in real-time with the administration of the diagnostic test. It is further surprising and unexpected that an ability to fast forward through "dead time" in the asynchronous administration and virtual proctoring disclosed herein shows such a significant reduction (e.g., reduced to 15% in Prophetic Example 2, reduced to 5% in Prophetic Example 3) in virtual proctor and proctor computer device requirements compared with live real-time virtual proctoring. Moreover, proctors in asynchronous administration and virtual proctoring are not coupled to a patient's schedule in order to proctor the diagnostic test administration.

Numerical ranges should be understood to include the endpoint values unless expressly disclosed to the contrary (e.g., from about X to about Y includes X and Y; between X and Y includes X and Y; greater than or less than X does not include value X). Moreover, each numerical range should be understood to include each numerical value falling between the endpoints (e.g., from 0.1 to 1 includes, 0.1 0.2, 0.3, 0.4, 0.5, 0.6, 0.7, 0.8, 0.9, and 1); greater than 1 includes 1, 2, 3, and so on). It is contemplated that express disclosure of terms such as comprises, contains, includes, having, and their grammatical variants provides support for narrower terms, including but not limited to consisting of and consisting essentially of.

Although the present disclosure and its advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, composition of matter, methods, and steps described in the specification. As one of ordinary skill in the art will readily appreciate from the disclosure, processes, machines, manufacture, compositions of matter, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, methods, or steps.

What is claimed is:

1. A method for asynchronous administration and virtual proctoring of a diagnostic test testing for a presence of a medical condition, comprising:
   receiving, by a computer system from an application running on a patient computer device, a video file and a first image file, wherein the video file contains a recording of a patient administering the diagnostic test, wherein the first image file is a photo of a medical device displaying a result of the diagnostic test;
   streaming, by the computer system to a proctor computer device, the video file, wherein streaming comprises playing a first portion of the recording in the video file in a speed at which the recording was recorded and a second portion comprising dead time in the recording in the video file in high speed; and
   receiving, by the computer system from the proctor computer device, a confirmation result of the diagnostic test, wherein the confirmation result contains a positive result, a negative result, or an inconclusive result of the medical condition;
   wherein the diagnostic test is a biopsy, a sports doping test, a blood pressure test, a CAT scan, a CT scan, a MRI scan, a pregnancy test, a diagnostic test for a bacteria, or a diagnostic test for a virus,
   wherein the dead time comprises a patient waiting for results after administration of the diagnostic test in the recording and a patient fumbling around with identification in the recording.

2. The method of claim 1, wherein the computer system does not receive the video file in a video stream from the patient computer device.

3. The method of claim 1, wherein the dead time of the recording on the video file is after administration of the diagnostic test and before the result is indicated on the medical device.

4. The method of claim 1, further comprising:
   sending, by the computer system to the proctor computer device, the first image file.

5. The method of claim 1, wherein a number of virtual proctors needed for asynchronous administration and virtual proctoring during a period of time for mass diagnostic testing is less than a number of virtual proctors needed for live real-time virtual proctoring during the period of time.

6. The method of claim 1, further comprising:
   sending, by the computer system to the application running on the patient computer device, a notification containing the confirmation result of the diagnostic test.

7. The method of claim 1, wherein the virus is a SARS-COV-2 virus or a variant of the SARS-COV-2 virus.

8. The method of claim 1, further comprising:
receiving, by the computer system from the application running on the patient computer device, a second image file containing a photo of an identification for the patient;
sending, by the computer system to the proctor computer device, the second image file; and
associating a patient identifier with the video file and with the first image file.

9. The method of claim 8, further comprising:
associating the patient identifier with the second image file.

10. The method of claim 1, wherein the recording of the video file is recorded beginning at a first point in time, wherein streaming begins at a second point in time, wherein the second point in time occurs after the first point in time.

11. The method of claim 1, wherein the recording of the video file is recorded beginning at a first point in time, wherein a virtual proctor views the recording and certifies the confirmation result based on the first image file in a continuous amount of time that begins after the first point in time and ends before the confirmation result is received by the computer system from the proctor computer device.

12. The method of claim 11, wherein the recording in the video file ends being recorded at a second point in time, wherein the continuous amount of time begins after the second point in time.

* * * * *